(12) United States Patent
Bochmann et al.

(10) Patent No.: US 7,238,819 B2
(45) Date of Patent: Jul. 3, 2007

(54) PROCESS FOR PREPARING ISOBUTYLENE-BASED POLYMERS

(75) Inventors: Manfred Bochmann, Norwich (GB); Mark Schormann, Norwich (GB); Shaun Garratt, Cosby (GB)

(73) Assignee: LANXESS Inc., Sarnia, Ontario (CA)

( * ) Notice: Subject to any disclaimer, the term of this patent is extended or adjusted under 35 U.S.C. 154(b) by 55 days.

(21) Appl. No.: 10/502,073

(22) PCT Filed: Jan. 21, 2003

(86) PCT No.: PCT/CA03/00067

§ 371 (c)(1),
(2), (4) Date: Apr. 5, 2005

(87) PCT Pub. No.: WO03/062284

PCT Pub. Date: Jul. 31, 2003

(65) Prior Publication Data

US 2005/0165182 A1    Jul. 28, 2005

(30) Foreign Application Priority Data

Jan. 21, 2002  (CA) .................................... 2368724

(51) Int. Cl.
C07F 7/00   (2006.01)
B01J 31/00  (2006.01)
C08F 4/06   (2006.01)

(52) U.S. Cl. .................. 556/12; 556/28; 526/120; 526/160; 526/339; 526/348.7; 502/152

(58) Field of Classification Search .............. 556/12, 556/28; 502/152; 526/160, 120, 339, 348.7
See application file for complete search history.

(56) References Cited

U.S. PATENT DOCUMENTS 4,910,321 A    3/1990  Kennedy et al. ............ 549/213

(Continued)

FOREIGN PATENT DOCUMENTS

EP    277 003    1/1988

(Continued)

OTHER PUBLICATIONS

Calderazzo et al., Journal of Organometallic Chemistry, vol. 518, No. 1-2, pp. 189-196 (1996).*

(Continued)

*Primary Examiner*—Porfirio Nazario-Gonzalez
(74) *Attorney, Agent, or Firm*—Jennifer R. Seng (57) ABSTRACT

This invention relates to a metal organic compound, a catalytic composition comprising said metal organic compound, a process for homo- or co-polymerizing isoolefines in the presence of said metal organic compound and a method of stabilizing a compound of the general structure (II) $[R'HC(CRR'')_2]^{2+}[M_2X_9]^-$, in which R is a group of the formula $SiR^1R^2R^3$, R'' is hydrogen, $C_1$ to $C_{12}$ alkyl, a $C_6$ to $C_{14}$ aryl or a $C_7$ to $C_{20}$ alkylaryl, M is Zr or Hf, X is a halogen atom, and $R^1$ to $R^3$ is a $C_1$ to $C_{12}$ alkyl group, with a compound R' of the formula $M'R^4R^5R^6$, in which M' is Si, Ge, Sn or Pb and $R^4$ to $R^6$ is a $C_1$ to $C_{12}$ alkyl group as well as a non-coordinating anion of the general structure $[M_2X_9]^-$ in which M is Zr or Hf and X is a halogen atom.

14 Claims, 2 Drawing Sheets

U.S. PATENT DOCUMENTS

| | | | |
|---|---|---|---|
| 4,929,683 A | 5/1990 | Kennedy et al. | 525/268 |
| 5,198,401 A | 3/1993 | Turner et al. | 502/155 |
| 5,448,001 A | 9/1995 | Baird | 526/134 |

FOREIGN PATENT DOCUMENTS

| | | |
|---|---|---|
| EP | 277 004 | 1/1988 |
| EP | 426 637 | 10/1990 |
| WO | 92/00333 | 1/1992 |
| WO | 00/04061 | 1/2000 |

OTHER PUBLICATIONS

J. Am. Chem. Soc. 1997, 119, pp. 3087-3092, Thomas Laube, George A. Olah, and Robert Bau; "First X-ray Crystallographic Study of a Benzyl Cation, Cumyl Hexafluoroantimonate (V), and Structural Implications".

Chem. Rev. 1998, 98, pp. 1277-1312, Thomas Laube; "Interactions between Carbocations and Anions in Crystals".

* cited by examiner

PROCESS FOR PREPARING ISOBUTYLENE-BASED POLYMERS

FIELD OF THE INVENTION

The present invention relates to a polymerisation process for the preparation of isobutylene-based polymers.

BACKGROUND OF THE INVENTION

Carbocations have long been regarded as important intermediates in organic reactions but are generally too unstable to be isolable.

Three types of carbocations have so far been isolated, and several of these have been structurally characterized by X-ray diffraction: (1) carbocations stabilized by heteroatoms in α-positions, notably O and N but including F and Cl; (2) carbocations with phenyl substituents; (3) tertiary-alkyl carbocations. These structural aspects have been summarized in *Interactions between carbocations and anions in crystals*. T. Laube, *Chem. Rev.* 1998, 98, 1277.

Carbocations carrying three alkyl substituents have proved isolable in several cases.

These include the parent ion $CMe_3^+$ as $Sb_2F_{11}^-$ salt (see: First X-ray crystallographic study of a benzyl cation, cumyl hexafluoroantimonate(V), and structural implications. T. Laube, G. A. Olah and R. Bau, *J. Am. Chem. Soc.* 1997, 119, 3087.) Low-temperature techniques are required to generate, crystallize and structurally characterize these compounds, which implies that their application is limited by their thermal instability and isolation techniques in $SbF_5$-based media.

None of these examples contains Si or Sn substituents.

Cationic polymerization of olefins is known in the art.

Conventionally, cationic polymerization is effected using a catalyst system comprising: (i) a Lewis acid, (ii) a tertiary alkyl initiator molecule containing a halogen, ester, ether, acid or alcohol group, and, optionally, (iii) an electron donor molecule such as ethyl acetate. Such catalysts systems have been used for the so-called "living" and "non-living" carbocationic polymerization of olefins.

Catalyst systems based on halogens and/or alkyl-containing Lewis acids, such as boron trichloride and titanium tetrachloride, use various combinations of the above components and typically have similar process characteristics. For the so-called "living" polymerization systems, it is conventional for Lewis acid concentrations to exceed the concentration of initiator sites by 16 to 40 times in order to achieve 100 percent conversion in 30 minutes (based upon a degree of polymerization equal to 890) at −75° to −80° C.

Examples of the so-called "living" polymerization systems are taught in U.S. Pat. No. 4,929,683 and U.S. Pat. No. 4,910,321, the contents of each of which are incorporated herein by reference. Specifically, these patents teach the use of Lewis acids in combination with organic acids, organic esters or organic ethers to form cationic polymerization initiators that also create a complex counter anion. Apparently, the complex counter anion does not assist in or cause proton elimination.

In the so-called "non-living" polymerization systems, high molecular weight polyisobutylenes are prepared practically only at low temperatures (−60 to −100° C.) and at catalyst concentrations exceeding one catalyst molecule per initiator molecule. In practice, many of these catalyst systems are applicable only in certain narrow temperature regions and concentration profiles.

In recent years, a new class of catalyst systems utilising compatible non-coordinating anions in combination with cyclopentadienyl transition metal compounds (also referred to in the art as "metallocenes") has been developed. See, for example, any one of:

published European patent application 0,277,003A;
published European patent application 0,277,004;
U.S. Pat. No. 5,198,401; and
published International patent application WO92/00333.

The use of ionising compounds not containing an active proton is also known. See, for example, any one of:

published European patent application 0,426,637A; and
published European patent application 0,573,403A.

U.S. Pat. No. 5,448,001 discloses a carbocationic process for the polymerization of isobutylene which utilizes a catalyst system comprising, for example, a metallocene catalyst and a borane.

WO-A 1-00/04061 discloses a cationic polymerization process which is conducted at subatmospheric pressure in the presence of a catalyst system such as $Cp*TiMe_3$ (the "initiator") and $B(C_6F_5)_3$ (the "activator"). Such a system generates a "reactive cation" and a "non-coordinating anion" (NCA). Using such a catalyst system a polymer having desirable molecular weight properties may be produced in higher yields and at higher temperatures than by conventional means, thus lowering capital and operating costs of the plant producing the polymer.

The wide range of NCAs disclosed in WO-A1-00/04061 includes, boron, phosphorus and silicon compounds, including borates and bridged di-boron species.

The polymerization of isobutylene with small amounts of isoprene, to produce butyl rubber, presents unique challenges. Specifically, as is well known in the art, this polymerization reaction is highly exothermic and it is necessary to cool the reaction mixture to approximately −95° C. in large scale production facilities. This requirement has remained, notwithstanding advances in the art relating to the development of novel reactor designs and/or novel catalyst systems.

Further, it is the case that the copolymers so produced have markedly lower molecular weights than homopolymers prepared under similar conditions. This is because the presence of isoprene in the monomer feed results in chain termination by β-H elimination.

It would be desirable to be able to obtain high molecular weight isobutylene-based polymers, and in particular isobutylene-based copolymers, in high yield, at relatively high temperatures (as compared to the methods of the art) and under more environmentally-friendly conditions. This has not been demonstrated to date.

SUMMARY OF THE INVENTION

We have found that a compound of the general structure (I)

$$[HC(CRR'R'')(CRR'R'')]^+[M_2X_9]^- \qquad (I),$$

in which

R is independantly hydrogen or a group of the formula $M'R^1R^2R^3$,
R' is a group of the formula $M'R^4R^5R^6$,
R'' is hydrogen, a $C_1$ to $C_{12}$ alkyl, a $C_6$ to $C_{14}$ aryl or a $C_7$ to $C_{20}$ alkylaryl,
M is Zr or Hf,
M' is Si, Ge, Sn or Pb,
X is a halogen atom, and $R^1$ to $R^6$ is a $C_1$ to $C_{12}$ alkyl group, a $C_6$ to $C_{14}$ aryl or a $C_7$ to $C_{20}$ alkylaryl, shows high catalytic activity in isobutene copolymerisations.

In one aspect, this invention relates to the a.m. compound of the general structure (I) in itself.

In another aspect, this invention relates to a catalyst of the general structure (I).

In still another aspect, this invention relates to a catalytic composition comprising a compound of the a.m. general structure (I).

In still another respect, this invention relates to a process for homo- or co-polymerizing isoolefines, optionally in the presence of further copolymerizable monomers, in the presence of a compound of the general structure (I).

In still another respect, this invention relates to a method of stabilizing a compound of the general structure (II)

$$[HC(CRR'')(CRR'R'')]^+[M_2X_9]^- \quad (II),$$

in which
R is a group of the formula $M'R^1R^2R^3$,
R'' is hydrogen, a $C_1$ to $C_{12}$ alkyl, a $C_6$ to $C_{14}$ aryl or a $C_7$ to $C_{20}$ alkylaryl,
M is Zr or Hf,
M' is Si, Ge, Sn or Pb
X is a halogen atom, and
$R^1$ to $R^3$ is a $C_1$ to $C_{12}$ alkyl group, with a compound R' of the formula $M'R^4R^5R^6$, in which M' is Si, Ge, Sn or Pb and $R^4$ to $R^6$ is a $C_1$ to $C_{12}$ alkyl group.

In still another respect, this invention relates to a non-coordinating anion of the general structure $[M_2X_9]^-$ in which M is Zr or Hf and X is a halogen atom.

BRIEF DESCRIPTION OF THE DRAWINGS

FIG. 1 illustrates the crystal structure of the cation in

FIG. 2 illustrates the crystal structure of the anion in

DETAILED DESCRIPTION OF THE INVENTION

Suitable $C_1$ to $C_{12}$ alkyls are known and include methyl, ethyl, linear or branched propyl, such as n-propyl, isopropyl, linear or branched butyl, such as n-butyl, sec. butyl, tert. butyl, linear or branched pentyl, linear or branched hexyl, linear or branched heptyl, linear or branched octyl, linear or branched nonyl and so on. It will be apparent to those skilled in the art, that said $C_1$ to $C_{12}$ alkyls may be saturated, single unsaturated or multiple unsaturated. Methyl and ethyl are preferred, methyl is especially preferred.

Suitable $C_5$ to $C_{14}$ aryl groups are well known and include cyclopentadienyl, phenyl, naphthenyl, fluorenyl anthracenyl or phenanthryl.

Suitable $C_7$ to $C_{20}$ alkylaryl groups are well known and include combinations of the mentioned $C_1$ to $C_{12}$ alkyls with the given $C_6$ to $C_{14}$ aryl groups such as benzyl, penta methyl cyclopentadienyl, substituted phenyl or fluorenyl groups as well as alkylaryl or arylalkyl groups not expressively mentioned in this invention.

Suitable halogen atoms include fluorine, chlorine, bromine, iodine and mixtures thereof.

It will be apparent to those skilled in the art that $R^1$ to $R^6$ may be the same or different and are chosen independently from each other.

Preferred are compounds of the general structure (Ia), in which R, R', M and X denote for the groups stated above.

Especially preferred are compounds of the general structure (Ib), in which R, R', and M denote for the groups stated above and $R^1$ to $R^6$ denote for methyl.

The inventive compounds of the general structure (I) may be used alone or in combination with catalysts/initiators commonly used in isoolefin (co)polymerisation processes. Such compounds are known and include dialkylaluminum halides, such as diethylaluminum chloride, monoalkylaluminum dihalides, such as isobutylaluminum dichloride, aluminoxanes, such as methylaluminoxane and mixtures thereof.

Of course, other catalyst systems, conventionally used to produce butyl polymers are useful herein—see, for example, "Cationic Polymerization of Olefins: A Critical Inventory" by Joseph P. Kennedy (John Wiley & Sons, Inc.® 1975), U.S. Pat. No. 2,356,128 and *Ullmanns Encyclopedia of Industrial Chemistry*, volume A 23, 1993, pages 288–295.

It might be advantageous to support the compounds of the invention on inert solid particular substances, such as silica, carbon-black, polyolefin beads or powders, such as PE or PP, metal oxides, such as magnesium chloride, calcium carbonate, sodium chloride, etc. Such preparations are another subject of the invention.

It will be apparent to the skilled in the art, that a mixture of different compounds claimed in this invention might be used to tailor the catalytic profile of the whole catalytic composition.

The compound(s) of the general structure (I) are useful as catalysts, especially in a process directed to the homo- or co-polymerization of isoolefins.

The compound(s) of the general structure (I) are particularly advantageous in the preparation of butyl rubber polymers. The terms "butyl rubber", "butyl polymer" and "butyl rubber polymer" are used throughout this specification interchangeably. The term "butyl rubber" as used throughout this specification is intended to denote polymers prepared by reacting a major portion, e.g., from 70 to 99.5 parts by weight, usually 85 to 99.5 parts by weight of an isoolefin, such as isobutylene, with a minor portion, e.g., 30 to 0.5 parts by weight, usually 15 to 0.5 parts by weight, of a multiolefin, e.g., a conjugated diolefin, such as isoprene or butadiene, for each 100 weight parts of these monomers reacted.

The isoolefin, in general, is a $C_4$ to CB compound, e.g., isobutylene, 2-methyl-1-butene, 3-methyl-1-butene, 2-methyl-2-butene and 4-methyl-1-pentene and mixtures thereof. The multiolefin, in general, is a $C_4$ to $C_{14}$ diene such as isoprene, butadiene, 2-methylbutadiene, 2,4-dimethylbutadiene, piperyline, 3-methyl-1,3-pentadiene, 2,4-hexadiene, 2-neopentylbutadiene, 2-methly-1,5-hexadiene, 2,5-dimethly-2,4-hexadiene, 2-methyl-1,4-pentadiene, 2-methyl-1,6-heptadiene, cyclopenta-diene, methylcyclopentadiene, cyclohexadiene, 1-vinyl-cyclohexadiene and mixtures thereof The preferred monomer mixture for use in the production of butyl rubber comprises isobutylene and isoprene. Optionally, one or more additional olefinic termonomer such as styrene, α-methylstyrene, p-methylstyrene, chlorostyrene, pentadiene and the like may be incorporated in the butyl rubber polymer. See, for example, any one of:

U.S. Pat. No. 2,631,984;
Canadian Application 2,316,741;
U.S. Pat. No. 5,162,445; and
U.S. Pat. No. 5,886,106.

Preferably, the process for producing the butyl polymer is conducted at a temperature conventional in the production of butyl polymers—e.g., in the range of from −120° C. to +50° C. The butyl polymer may be produced by polymerization in solution or by a slurry polymerization method. Polymerization is preferably conducted in suspension (the slurry method)—see, for example, Ullmann's Encyclopedia of Industrial Chemistry (Fifth, Completely Revised Edition, Volume A23; Editors Elvers et al.,).

Inert solvents or diluents known to the person skilled in the art for butyl polymerization may be considered as the solvents or diluents (reaction medium). These comprise alkanes, chloroalkanes, cycloalkanes or aromatics, which are frequently also mono- or polysubstituted with halogens. Hexane/chloroalkane mixtures, methyl chloride, dichloromethane or the mixtures thereof may be mentioned in particular. Chloroalkanes are preferably used in the process according to the present invention.

As an example, in one embodiment the process is conducted in the presence of an aliphatic hydrocarbon diluent, such as n-hexane, and a catalyst mixture comprising a compound of the general formula (I) as stated above.

Polymerization may be performed both continuously and discontinuously. In the case of continuous operation, the process is preferably performed with the following three feed streams:

I) solvent/diluent+isoolefin (preferably isobutene)
II) multiolefin (preferably diene, isoprene)
III) catalyst (comprising a compound of the general formula (I))

In the case of discontinuous operation, the process may, for example, be performed as follows:

The reactor, precooled to the reaction temperature, is charged with solvent or diluent and the monomers. The catalyst (comprising compound of the general formula (I)), optionally together with a catalyst customary in the field of butyl polymerization, is then pumped in the form of a dilute solution in such a manner that the heat of polymerization may be dissipated without problem. The course of the reaction may be monitored by means of the evolution of heat. All operations are performed under protective gas. Once polymerization is complete, the reaction may be terminated with a phenolic antioxidant, such as, for example, 2,2'-methylenebis(4-methyl-6-tert.-butylphenol), dissolved in ethanol.

If it is desired to produce a halogenated butyl polymer, the butyl polymer prepared according to the above process may be halogenated in a conventional manner. See, for example, U.S. Pat. No. 5,886,106. Thus, the halogenated butyl rubber may be produced either by treating finely divided butyl rubber with a halogenating agent such as chlorine or bromine, or by producing brominated butyl rubber by the intensive mixing, in a mixing apparatus, of brominating agents such as N-bromosuccinimide with a previously made butyl rubber. Alternatively, the halogenated butyl rubber may be produced by treating a solution or a dispersion in a suitable organic solvent of a previously made butyl rubber with corresponding brominating agents. See, for more detail, Ullmann's Encyclopedia of Industrial Chemistry (Fifth, Completely Revised Edition, Volume A23; Editors Elvers et al.). The amount of halogenation during this procedure may be controlled so that the final terpolymer has the preferred amounts of halogen described hereinabove. The pressure under which the polymerizations take place is not important and may usually be in the range of from 0.01 to 1000 bar.

The compound of the general structure (I) may be prepared by admixture of [HC(CRR")(CRR'R")] with $MX_4$ in the presence of R'X in a inert solvent, in which
R is a group of the formula $M'R^1R^2R^3$,
R' is a group of the formula $M'R^4R^5R^6$,
R" is hydrogen, a $C_1$ to $C_{12}$ alkyl, a $C_6$ to $C_{14}$ aryl or a $C_7$ to $C_{20}$ alkylaryl,
M is Zr or Hf.
M' is Si, Ge, Sn or Pb,
X is a halogen atom, and
$R^1$ to $R^6$ is a $C_1$ to $C_{12}$ alkyl group, a $C_6$ to $C_{14}$ aryl or a $C_7$ to $C_{20}$ alkylaryl.

The R' is to be in β-position to the central carbon atom, as it is apparent from the above structure.

The nature of the inert solvent is not crucial, however, halogenalkanes, such as chloroalkanes, especially dichloromethane are preferred.

The stabilization of the final compound with one or more R' is crucial for the preparation. To our knowledge, this is the very first isolated secondary-alkyl carbocation ever. Therefore, said method of stabilizing a secondary-alkyl cation with a group of the general formula $[M'R^4R^5R^6]^+$ in which M' and $R^4$ to $R^6$ denote for the atoms/groups stated above is another subject of the present invention.

Yet another subject of the present invention, is a metalorganic compound comprising a non-coordinating anion of the general structure $[M_2X_9]^-$ in which M is Zr or Hf and X is a halogen atom and a method of homo- or copolymerizing an olefin in the presence of a compound comprising an anion of the general structure $[M_2X_9]^-$ in which M is Zr or Hf and X is a halogen atom. Although the present invention is focussed on the homo- or copolymerization of isoolefins as stated above, it will be apparent to, the skilled in the art that other olefins, such as ethylene, propylene, butene, octene and so on, will also polymerize in the presence of a compound comprising an anion of the general structure $[M_2X_9]^-$ in which M is Zr or Hf and X is a halogen atom.

It will be apparent to those skilled in the art that the anion $[M_2X_9]^-$ may be exchanged for other anions, notably so called "non-coordinating" anions of the type $[R"E(C_6F_6)_3]^-$, $[E(C_6F_6)_4]^-$, $[E'-Z-E"]^{n-}$, in which each R" is independently hydrogen, a $C_1$ to $C_{12}$ alkyl, a $C_6$ to $C_{14}$ aryl or a $C_7$ to $C_{20}$ alkylaryl, each E is independently B or Al, E' and E" are independently Lewis acidic B and Al compounds, preferably $E(C_6F_6)_3$, and Z is a bridging group such as CN, $N_3$, OCN, $NH_2$, OH, OR, SR, $NR_2$, $PR_2$, and the like.

Therefore compounds comprising a cation of the general structure (III)

[HC(CRR'R")(CRR'R")]$^+$          (III), in which
R is independantly hydrogen or a group of the formula $M'R^1R^2R^3$,
R' is a group of the formula $M'R^4R^5R^6$,
R" is hydrogen, a $C_1$ to $C_{12}$ alkyl, a $C_6$ to $C_{14}$ aryl or a $C_7$ to $C_{20}$ alkylaryl,
M' is Si, Ge, Sn or Pb, and
$R^1$ to $R^6$ is a $C_1$ to $C_{12}$ alkyl group, a $C_6$ to $C_{14}$ aryl or a $C_7$ to $C_{20}$ alkylaryl, is another object of the invention.

Embodiments of the present invention will be described with reference to the following examples, which are provided for illustrative purposes only and should not be used to limit the scope of the invention.

EXAMPLES

All glassware was dried by heating at 120° C. for at least 12 hours before being assembled. Nitrogen was purified by passing sequentially over heated BASF catalyst and molecular sieves. Dichloromethane was dried by refluxing over calcium hydride under nitrogen, toluene by refluxing over sodium-benzophenone under nitrogen, and both solvents were freshly distilled and then freeze-pump-thaw degassed prior to use. When necessary, solvents were stored over activated molecular sieves under nitrogen.

The diene monomer isoprene (IP) was purified by passing through a column to remove p-tertbutylcatechol, titrated with n-BuLi (1.6 M solution in hexanes) and distilled under vacuum prior to use. This was then stored at −30° C. in a nitrogen filled dry box.

Isobutylene (IB) was purified and dried by passing through columns of 10 wt % Na on $Al_2O_3$ and appropriate mol-sieves and condensed directly into the reaction vessel.

Example 1

Synthesis of $[CH\{CH(SiMe_3)(SnMe_3)\}_2]^+Zr_2Cl_9^-$

All the manipulations have been carried out under strict exclusion of oxygen and moisture in a nitrogen inert atmosphere. A solution of $Me_3SnCl$ (0.6 g, 3.0 mmol) and $Me_3SiCH=CHCH(SiMe_3)(SnMe_3)$ (1.0 g, 2.9 mmol) in $CH_2Cl_2$ (30 mL) was transferred to $ZrCl_4$ (1.4 g, 6.0 mmol). On stirring for 4 h at room temperature the solid dissolved and the solution turned yellow. After filtration the amount of solvent was reduced to 10 mL. Crystallization at −30° C. afforded the title compound in ca 50% yield, mp. 109° C. Solid state magic-angle spinning $^{13}C$ NMR (relative to tetramethylsilane): δ −1, 0, 3 ($SiMe_3$, $SnMe_3$); 70 (CH); 217 ($CH^+$), $^{29}Si$ NMR: δ 1 ppm.

Example 2

Synthesis of $[CH\{CH(SiMe_3)(SnMe_3)\}_2]^+Hf_2Cl_9^-$

Following the method of Example 1, a solution of $Me_3SnCl$ (0.6 g, 3.0 mmol) and $Me_3SiCH=CHCH(SiMe_3)(SnMe_3)$ (1.0 g, 2.9 mmol) in $CH_2Cl_2$ (30 mL) was transferred to $HfCl_4$ (6.0 mmol). On stirring for 4 h at room temperature the solid dissolved and the solution turned yellow. After filtration the amount of solvent was reduced to 10 mL. Crystallization at −30° C. afforded the title compound in ca. 50% yield, mp. 120° C. The $^{13}C$ and $^{29}Si$ solid-state NMR spectroscopic data were essentially identical to Example 1.

Figure 1:
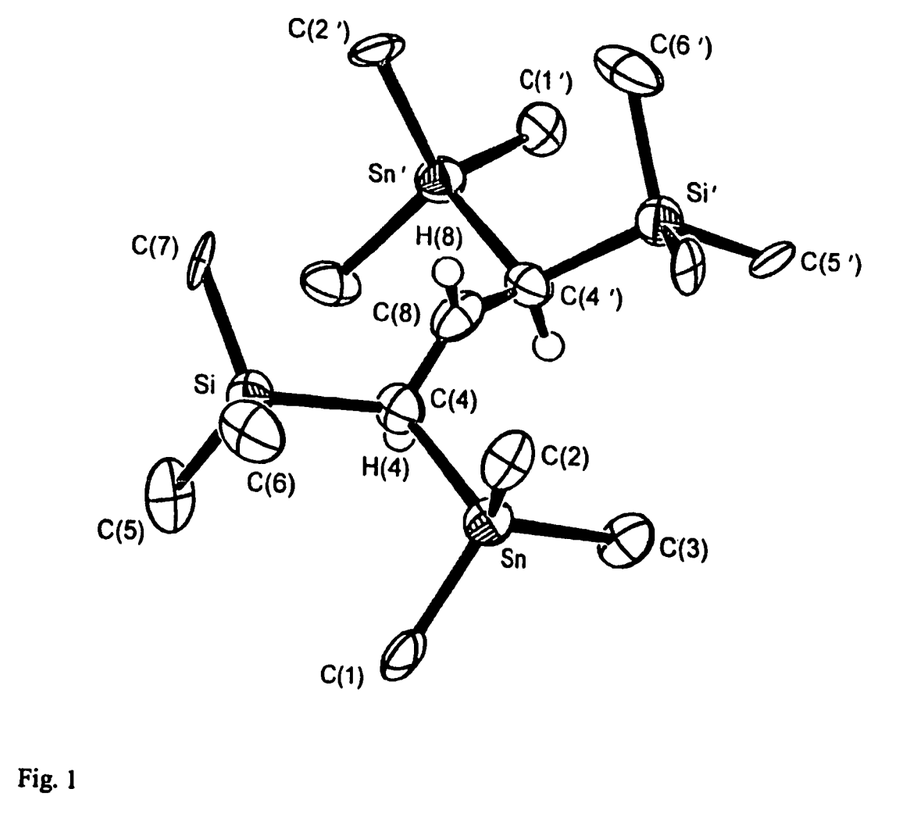
Figure 2:
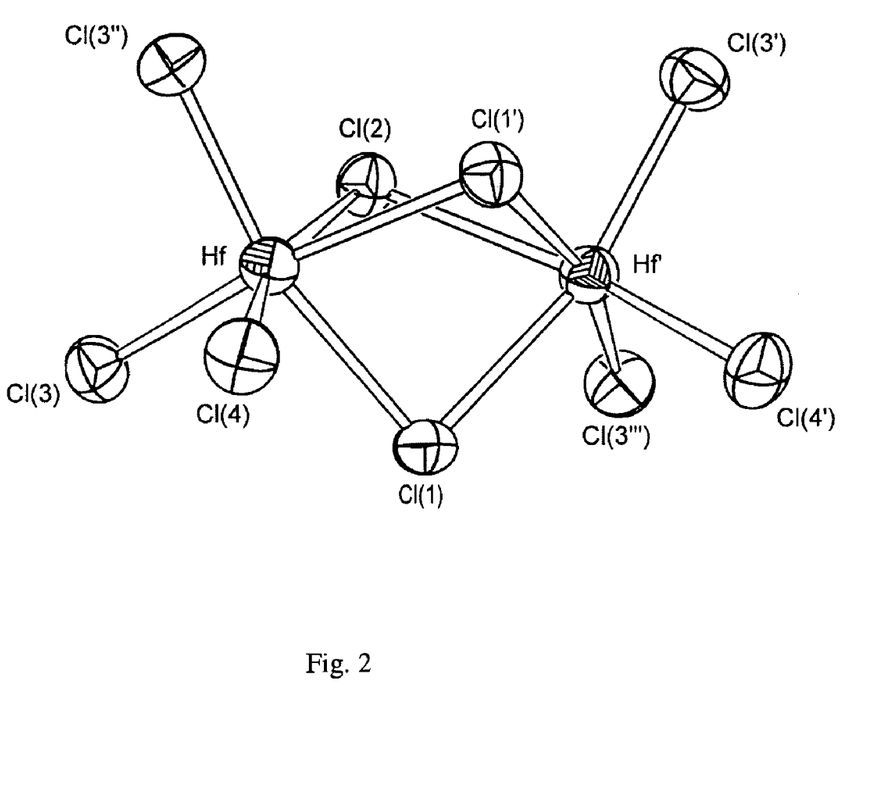

FIG. 1 shows the crystal structure of the cation in $[CH\{CH(SiMe_3)(SnMe_3)\}_2]^+Hf_2Cl_9^-$, FIG. 2 shows the crystal structure of the anion in $[CH\{CH(SiMe_3)(SnMe_3)\}_2]+Hf_2Cl_9$.

Example 3

Isobutene Polymerization

Into a 250 mL 3-necked reaction flask, equipped with a magnetic follower and cooled to −78° C. with a dry ice/acetone bath, was condensed 100 mL of isobutene (dried by passing through 10 percent weight sodium on aluminum oxide and 4A molecular sieves). 30 mg (30 μmol) of $[HC\{CH(SiMe_3)(SnMe_3))_2]^+[Zr_2Cl_9]^-$ was dissolved in 2 mL of dichloromethane. This initiator solution was then transferred to the rapidly stirred (1000/min) isobutene (still cooled to −78° C.), via syringe under positive nitrogen pressure. The mixture was stirred for 3 minutes, until a significant increase in viscosity was observed. At this point, the reaction was terminated by addition of methanol (10 mL). The reaction mixture was poured into methanol (200 mL) to precipitate the polymer. The excess monomer was allowed to evaporate, the solvent decanted, then the polymer was dried in an oven at 50° C. to constant weight. The yield of polyisobutene was 3.6 g, $M_n$=160,000 and $M_w$=233,000.

Example 4

Isobutene/Isoprene Copolymerization

The methodology of Example 3 was repeated, except that 1.5 mL of isoprene was added to the reaction vessel prior to initiation. The mixture was allowed to stir at −78° C. for 10 minutes, before addition of methanol (10 mL) to terminate the reaction. The yield of copolymer was 5.5 g ($M_n$=104,000, $M_w$=203,000). The isoprene content in the rubber was 1.5 mol-percent.

Example 5

Into a 250 mL 3-necked reaction flask, equipped with a magnetic follower and cooled to −78° C. with a dry ice/acetone bath, was condensed 100 mL of isobutene (dried by passing through 10 percent weight sodium on aluminum oxide and 4A molecular sieves). Isoprene (1.5 mL) was added via syringe. 36 mg (30 μmol) of $[HC\{CH(SiMe_3)(SnMe_3)\}_2]^+[Hf_2Cl_9]^-$ was dissolved in 2 mL of dichloromethane. This initiator solution was then transferred to the rapidly stirred (1000/min) isobutene (still cooled to −78° C.), via syringe under positive nitrogen pressure. The mixture was stirred for 10 minutes, then terminated by addition of methanol (10 mL). The reaction mixture was poured into methanol (200 mL) to precipitate the polymer. The excess monomer was allowed to evaporate, the solvent decanted, then the polymer was dried in an oven at 50° C. to constant weight. The yield of copolymer was 7.3 g, $M_n$=124,200, $M_w$=258,800 and the isoprene content in the rubber was 1.2 mol-percent.

Example 6

The methodology of Example 5 was repeated, except that 3 mL of isoprene were added to the reaction mixture. The yield after 10 minutes reaction was 2.5 g, $M_n$=144,000, $M_w$=312,000 and the isoprene content in the rubber was 2.6 mol-percent.

Example 7

The methodology of Example 5 was repeated, except that 5 mL of isoprene were added to the reaction mixture. The yield after 15 minutes reaction was 4.4 g, $M_n$=125,000, $M_w$=205,000 and the isoprene content in the rubber was 4.0 mol-percent.

Example 8

Into a 250 mL 3-necked reaction flask, equipped with a magnetic follower and cooled to −50° C., was condensed 100 mL of isobutene (dried by passing through 10 percent weight sodium on aluminum oxide and 4A molecular sieves). Isoprene (1.5 mL) was added via syringe. 18 mg (15

μmol) of [HC{CH(SiMe$_3$)(SnMe$_3$)}$_2$]$^+$[Hf$_2$Cl$_9$]$^-$ was dissolved in 1.5 mL of dichloromethane. This initiator solution was then transferred to the rapidly stirred (1000/min) isobutene (still cooled to −50° C.), via syringe under positive nitrogen pressure. Polymerization ensued rapidly and the reaction was terminated after 30 seconds by addition of methanol (10 mL). The reaction mixture was poured into methanol (200 mL) to precipitate the polymer. The excess monomer was allowed to evaporate, the solvent decanted, then the polymer was dried in an oven at 50° C. to constant weight. The yield of copolymer was 4.5 g, M$_n$=108,000, M$_w$=179,000 and the isoprene content in the rubber was 1.4 mol-percent.

Example 9

Into a 250 mL 3-necked reaction flask, equipped with a magnetic follower and cooled to −35° C., was condensed 100 mL of isobutene (dried by passing through 10 percent weight sodium on aluminum oxide and 4A molecular sieves). Isoprene (1.5 mL) was added via syringe. 12 mg (10 μmol) of [HC{CH(SiMe$_3$)(SnMe$_3$)}$_2$]$^+$[Hf$_2$Cl$_9$]$^-$ was dissolved in 1.5 mL of dichloromethane. This initiator solution was then transferred to the rapidly stirred (1000/min) isobutene (still cooled to −35° C.), via syringe under positive nitrogen pressure. Polymerization ensued rapidly and the reaction was terminated after 2 minutes by addition of methanol (10 mL). The reaction mixture was poured into methanol (200 mL) to precipitate the polymer. The excess monomer was allowed to evaporate, the solvent decanted, then the polymer was dried in an oven at 50° C. to constant weight. The yield of copolymer was 4.6 g, M$_n$=73,000, M$_w$=125,000 and the isoprene content in the rubber was 1.1 mol-percent.

Example 10

An initiator stock solution was prepared by addition of 70 mg (0.2 mmol) of (SiMe$_3$)CH=CH(SiMe$_3$)(SnMe$_3$) in dichloromethane (10 mL) and 38 mg (0.2 mmol) of Me$_3$SnCl in dichloromethane (10 mL) to 93 mg (0.4 mmol) of freshly sublimed ZrCl$_4$. This mixture was stirred for five hours at room temperature, resulting in a yellow-colored solution. Into a 250 mL 3-necked reaction flask, equipped with a magnetic follower and cooled to −78° C., was condensed 100 mL of isobutene (dried by passing through 10 percent weight sodium on aluminum oxide and 4A molecular sieves). Isoprene (1.5 mL) was added via syringe. A 4 μL aliquot (40 μmol) of the initiator solution was transferred to the rapidly stirred (1000/min) isobutene (still cooled to −78° C.), via syringe under positive nitrogen pressure.

Polymerization ensued steadily and the reaction was terminated after 5 minutes by addition of methanol (10 mL). The reaction mixture was poured into methanol (200 mL) to precipitate the polymer. The excess monomer was allowed to evaporate, the solvent decanted, then the polymer was dried in an oven at 50° C. to constant weight.

The yield of copolymer was 4.5 g, M$_n$=197,000, M$_w$=281,000 and the isoprene content in the rubber was 1.1 mol-percent.

Example 11

Dichloromethane (8 mL) and α-methyl-styrene (5 mL, 4.55 g) were charged into a 50 mL reaction vessel equipped with a magnetic follower, then cooled to −78° C. 30 mg (30 μmol) of [HC{CH(SiMe$_3$)(SnMe$_3$)}$_2$]$^+$[Zr$_2$Cl$_9$]$^-$ in 3 mL of dichloromethane was then transferred to the rapidly stirred solution via syringe. After 10 minutes a viscous gel had formed and the reaction was terminated by addition of methanol (5 mL). The product was poured into methanol (200 mL) to precipitate the polymer, stirred for 30 minutes then filtered, washing with methanol. The polymer was dried in an oven at 50° C. to constant weight. The yield of poly(α-methyl-styrene) was 4.1 g, M$_n$=23,700 and M$_w$=68,200.

Example 12

Dichloromethane (8 mL) and α-methyl-styrene (5 mL, 4.55 g) were charged into a 50 mL reaction vessel equipped with a magnetic follower, then cooled to −40° C. 30 mg (30 μmol) of [HC{CH(SiMe$_3$)(SnMe$_3$)}$_2$]$^+$[Zr$_2$Cl$_9$]$_g$ in 3 mL of dichloromethane was then transferred to the rapidly stirred solution via syringe. After 30 minutes a viscous gel had formed and the reaction was terminated by addition of methanol (5 mL). The product was poured into methanol (200 mL) to precipitate the polymer, stirred for 30 minutes then filtered, washing with methanol. The polymer was dried in an oven at 50° C. to constant weight. The yield of poly(α-methyl-styrene) was 4.22 g, M$_n$=13,900 and M$_w$=39,900.

Example 13

Isoprene (5 mL, 3.4 g) was charged into a 50 mL reaction vessel equipped with a magnetic follower, then cooled to −78° C. 30 mg (30 μmol) of [HC{CH(SiMe$_3$)(SnMe$_3$)}$_2$]$^+$[Zr$_2$Cl$_9$]$^-$ in 3 mL of dichloromethane was then transferred to the rapidly stirred monomer via syringe. The reaction was terminated after 4 minutes by addition of methanol (5 mL), when the medium became too viscous to allow stirring. The product was poured into methanol (200 mL) to precipitate the polymer, stirred for 30 minutes then filtered, washing with methanol. The polymer was dried in an oven at 50° C. to constant weight. The yield of polyisoprene was 1.0 g.

Example 14

Isoprene (5 mL, 3.4 g) and dichloromethane (3 mL) was charged into a 50 mL reaction vessel equipped with a magnetic follower, then cooled to −40° C. 30 mg (30 μmol) of [HC{CH(SiMe$_3$)(SnMe$_3$)}$_2$]$^+$[Zr$_2$Cl$_9$]$^-$ in 3 mL of dichloromethane was then transferred to the rapidly stirred monomer via syringe. The reaction was terminated after 10 minutes by addition of methanol (5 mL), when the medium became too viscous to allow stirring. The product was poured into methanol (200 mL) to precipitate the polymer, stirred for 30 minutes then filtered, washing with methanol. The polymer was dried in an oven at 50° C. to constant weight. The yield of polyisoprene was 1.0 g.

Examples 15 to 24 show results for polymerizations of isobutene alone and isobutene isoprene mixtures using different [HC{CH(SiMe$_3$)(SnMe$_3$)}$_2$]$^+$[M$_2$Cl$_9$]$^-$ initiators with M=Zr,Hf.

Examples 25 to 35 show results for polymerizations of isobutene isoprene mixtures using in-situ generated Me$_3$SiCH=CHCH(SiMe$_3$)(MMe$_3$)/Me$_3$SnCl/ZrCl$_4$ initiators (M=Si, Sn).

Polymerization Results
[HC{CH(SiMe$_3$)(SnMe$_3$)}$_2$]$^+$[M$_2$Cl$_9$]$^-$ initiator
100 mL isobutene, [init] = 10 μmol/mL in CH$_2$Cl$_2$

| Exp. No. | M | [Init] μmol | Isoprene mL | Temp °C. | Time min | Polymer yield/g | $M_w$/ $10^5$ g mol$^{-1}$ | $M_n$/ $10^5$ g mol$^{-1}$ | $M_w/M_n$ | Isoprene Incorporation mol-% |
|---|---|---|---|---|---|---|---|---|---|---|
| 15 | Zr | 30 | 0 | −78 | 3 | 3.6 | 2.33 | 1.60 | 1.5 | — |
| 16 | Zr | 30 | 1.5 | −78 | 10 | 5.5 | 2.03 | 1.04 | 2.0 | 1.5 |
| 17 | Zr | 25 | 1.5 | −50 | 10 | 3.0 | 4.80 | 2.72 | 1.8 | 1.2 |
| 18 | Hf | 12 | 0 | −50 | 1 | 2.4 | 3.48 | 1.29 | 2.6 | — |
| 19 | Hf | 30 | 1.5 | −78 | 10 | 7.3 | 2.59 | 1.24 | 2.1 | 1.2 |
| 20 | Hf | 30 | 3 | −78 | 10 | 2.5 | 3.12 | 1.44 | 2.2 | 2.6 |
| 21 | Hf | 30 | 5 | −78 | 15 | 4.4 | 2.05 | 1.25 | 1.6 | 4.0 |
| 22 | Hf | 15 | 1.5 | −50 | 0.5 | 4.5 | 1.79 | 1.08 | 1.7 | 1.4 |
| 23 | Hf | 15 | 3 | −50 | 3 | 5.6 | 1.88 | 1.06 | 1.8 | 1.3 |
| 24 | Hf | 10 | 1.5 | −35 | 10 | 3.3 | 1.44 | 0.77 | 1.9 | 1.2 |

Polymerizations with in-situ generated activators
Me$_3$SiCH=CHCH(SiMe$_3$)(MMe$_3$)/Me$_3$SnCl/ZrCl$_4$ initiator (M = Si, Sn)
100 mL isobutene, 1.5 mL isoprene, [init] = 10 μmol/mL in CH$_2$Cl$_2$

| Exp. No. | M | Mixing time of init (hrs) | [Init] μmol | Temp °C. | Time Min | Polymer Yield g | $M_w$/$10^5$ g mol$^{-1}$ | $M_n$/$10^5$ g mol$^{-1}$ | $M_w/M_n$ | Isoprene Incorporation % | Comments |
|---|---|---|---|---|---|---|---|---|---|---|---|
| 25 | Sn | 1.5 | 30 | −78 | 15 | 1.2 | 1.26 | 0.85 | 1.5 | 1.2 | Suspension |
| 26 | Sn | 3 | 30 | −78 | 15 | 2.0 | 0.83 | 0.43 | 1.9 | 1.3 | Suspension |
| 27 | Sn | 6 | 25 | −50 | 3 | 3.8 | 1.46 | 0.59 | 2.5 | 1.3 | Suspension |
| 28 | Sn | 7 | 20 | −35 | 3 | 3.6 | 0.95 | 0.53 | 1.8 | 1.3 | Suspension |
| 29 | Si | 3 | 40 | −78 | 1 | 5.8 | 1.42 | 0.88 | 1.6 | 1.2 | Suspension |
| 30 | Si | 4 | 30 | −78 | 10 | 5.3 | 1.29 | 0.69 | 1.9 | 1.3 | Suspension |
| 31 | Si | 5 | 20 | −50 | 10 | 4.3 | 1.23 | 0.68 | 1.8 | 1.4 | Suspension |
| 32 | Si | 6 | 20 | −50 | 15 | 3.5 | 1.85 | 1.21 | 1.5 | 1.4 | Suspension |
| 33 | Si | 22 | 30 | −78 | 15 | 5.5 | 3.07 | 1.18 | 2.6 | 1.4 | Solution used |
| 34 | Si | 23 | 20 | −50 | 15 | 3.0 | 1.54 | 0.52 | 3.0 | 1.2 | Solution used |
| 35 | Si | 24 | 20 | −35 | 15 | 3.8 | 1.40 | 0.40 | 3.5 | 1.3 | Solution used |

The invention claimed is:

1. A compound of the general structure (I)

[HC(CRR'R")(CRR'R")]$^+$[$M_2$X$_g$]$^-$      (I), wherein

R is independently hydrogen or a group of the formula M'R$^1$R$^2$R$^3$,

R' is a group of the formula M'R$^4$R$^5$R$^6$,

R" is hydrogen, a C$_1$ to C$_{12}$ alkyl, a C$_6$ to C$_{14}$ aryl or a C$_7$ to C$_{20}$ alkylaryl, M is Zr or Hf, M' is Si, Ge, Sn or Pb, X is a halogen atom, and R$^1$ to R$^6$ is a C$_1$ to C$_{12}$ alkyl group, a C$_6$ to C$_{14}$ aryl or a C$_7$ to C$_{20}$ alkylaryl.

2. A compound according to claim 1 wherein M' is Si or Sn.

3. A compound according to claim 1 with the general structure (Ia)

[HC(CHRR')$_2$]$^+$[M$_2$X$_9$]$^{31}$      (Ia), wherein

R is a group of the formula SiR$^1$R$^2$R$^3$,

R' is a group of the formula M'R$^4$R$^5$R$^6$,

R" is hydrogen, a C$_1$ to C$_{12}$ alkyl, a C$_6$ to C$_{14}$ aryl or a C$_7$ to C$_{20}$ alkylaryl, M is Zr or Hf, M' is Si, Ge, Sn or Pb, X is a halogen atom, and R$^1$ to R$^6$ is a C$_1$ to C$_{12}$ alkyl group, a C$_{6\,to\,C14}$ aryl or a C$_7$ to C$_{20}$ alkylaryl.

4. A compound according to claim 1 with the general structure (Ib)

[HC(CHRR')$_2$]$^+$[M$_2$Cl$_9$]$^{31}$      (Ib), wherein

R$^1$ to R$^6$ denote for methyl.

5. A catalyst of the general structure (I) according to claim 1.

6. A catalytic composition comprising a compound of the general structure (I) according to claim 1.

7. A process for homo- or co-polymerizing isoolefines, comprising polymerizing at least one isoolefin, optionally in the presence of further copolymerizable monomers, in the presence of a compound of the general structure (I) according to claim 1.

8. A process according to claim 7, wherein the isoolefin is isobutene.

9. A process according to claim 7, comprising polymerizing isobutene and isoprene.

10. A process according to claim 8, further comprising the presence of one or more co-polymerizable monomers.

11. A process according to claim 9, further comprising the presence of one or more co-polymerizable monomers.

12. A method of homo- or copolymerizing an olefin comprising polymerizing an olefin in the presence of a compound comprising an anion of the general structure $[M^2X_9]^{3-}$ in which M is Zr or Hf and X is a halogen atom.

13. A compound comprising a cation of the general structure (III)

$$[HC(CRR'R'')(CRR'R'')]^+ \qquad (III),$$

wherein R is independently hydrogen or a group of the formula $M'R^1R^2R^3$,

R' is a group of the formula $M'R^4R^5R^6$,

R" is hydrogen, a $C_1$ to $C_{12}$ alkyl, a $C_6$ to $C_{14}$ aryl or a $C_7$ to $C_{20}$ alkylaryl, M' is Si, Ge, Sn or Pb, and $R^1$ to $R^6$ is a $C_1$ to $C_{12}$ alkyl group, a $C_6$ to $C_{14}$ aryl or a $C_7$ to $C_{20}$ alkylaryl.

14. A method of stabilizing a compound of the general structure (II)

$$[HC(CRR'R'')(CRR'R'')]^+[M_2X_9]^{3-} \qquad (II),$$

in which

R is a group of the formula $M'R^1R^2R^3$,

R" is hydrogen, a $C_1$ to $C_{12}$ alkyl, a $C_6$ to $C_{14}$ aryl or a $C_7$ to $C_{20}$ alkylaryl, M is Zr or Hf, M' is Si, Ge, Sn or Pb X is a halogen atom, and R' to $R^3$ is a $C^1$ to $C^{12}$ alkyl group, comprising stabilizing a compound of the general structure (II) with a compound R' of the formula $M'R^4R^5R^6$, in which M' is Si, Ge, Sn or Pb and $R^4$ to $R^6$ is a $C_1$ to $C_{12}$ alkyl group.

* * * * *